United States Patent
Israel et al.

(10) Patent No.: US 10,987,196 B2
(45) Date of Patent: Apr. 27, 2021

(54) DRILL GUIDE

(71) Applicant: PALTOP ADVANCED DENTAL SOLUTIONS LTD., Caesarea (IL)

(72) Inventors: Or Israel, Tel Aviv (IL); Michael Klein, Maale Adumim (IL); Mordechai Mor Miles, Pardesiya (IL); Shlomo Hillel, Petach Tiqva (IL)

(73) Assignee: PALTOP ADVANCED DENTAL SOLUTIONS LTD., Caesarea (IL)

( * ) Notice: Subject to any disclaimer, the term of this patent is extended or adjusted under 35 U.S.C. 154(b) by 349 days.

(21) Appl. No.: 16/020,332

(22) Filed: Jun. 27, 2018

(65) Prior Publication Data

US 2020/0000550 A1  Jan. 2, 2020

(51) Int. Cl.
| | |
|---|---|
| *A61C 1/08* | (2006.01) |
| *A61C 8/00* | (2006.01) |
| *B23B 45/00* | (2006.01) |
| *A61C 3/02* | (2006.01) |
| *A61B 90/00* | (2016.01) |

(52) U.S. Cl.
CPC .......... *A61C 1/084* (2013.01); *A61B 2090/033* (2016.02); *A61C 3/02* (2013.01); *A61C 8/0089* (2013.01); *B23B 45/003* (2013.01)

(58) Field of Classification Search
CPC .......... A61C 1/082; A61C 1/084; A61C 3/02; A61C 8/0089; A61B 2090/033; A61B 17/176; B32B 45/003
See application file for complete search history.

(56) References Cited

U.S. PATENT DOCUMENTS

| | | | |
|---|---|---|---|
| 3,590,232 | A | 6/1971 | Sadowski |
| 4,468,200 | A | 8/1984 | Munch |
| 4,738,623 | A | 4/1988 | Driskell |
| 5,000,686 | A | 3/1991 | Lazzara et al. |

(Continued)

FOREIGN PATENT DOCUMENTS

| | | |
|---|---|---|
| FR | 2880534 | 7/2006 |
| WO | 2000/032134 | 6/2000 |

(Continued)

OTHER PUBLICATIONS

An Office Action dated Jan. 28, 2019, which issued during the prosecution of U.S. Appl. No. 15/845,103.

(Continued)

*Primary Examiner* — Heidi M Eide
(74) *Attorney, Agent, or Firm* — Sughrue Mion, PLLC

(57) ABSTRACT

Apparatus is provided for use with a dental handpiece, an oral surgical guide, and a bushing disposed in the oral surgical guide. The apparatus includes a drill bit having, a shank and a rigid guide-sleeve. A proximal end of the guide-sleeve couples to the dental handpiece, such that a lumen of the guide-sleeve and a drill bit coupled to the dental handpiece are coaxial along a central longitudinal axis of the drill bit. An inner diameter of the guide-sleeve is 0.03-0.06 mm greater than a diameter of the shank. The distal end of the guide-sleeve is slidably couplable with the bushing, such that upon the guide-sleeve being advanced into the bushing the dental handpiece is forced to align the axis of the drill bit to be coaxial with a central longitudinal axis of the bushing. Other applications are also described.

11 Claims, 9 Drawing Sheets

(56) References Cited

U.S. PATENT DOCUMENTS

| | | |
|---|---|---|
| 5,092,771 A | 3/1992 | Tatum |
| 5,105,690 A | 4/1992 | Lazzara et al. |
| 5,813,858 A | 9/1998 | Singer |
| 5,871,486 A | 2/1999 | Huebner et al. |
| 5,876,204 A | 3/1999 | Day et al. |
| 5,897,319 A | 4/1999 | Wagner et al. |
| 6,062,856 A | 5/2000 | Sussman |
| 6,174,167 B1 | 1/2001 | Wohrle |
| 6,283,754 B1 | 9/2001 | Wohrle |
| 6,342,057 B1 | 1/2002 | Brace et al. |
| 6,971,877 B2 | 12/2005 | Harter |
| 7,597,557 B2 | 10/2009 | Fromovich et al. |
| 7,677,891 B2 | 3/2010 | Niznick |
| 8,021,154 B2 | 9/2011 | Holzner et al. |
| 8,087,935 B2 | 1/2012 | Beaty et al. |
| 8,197,255 B2 | 6/2012 | Fromovich et al. |
| 8,483,857 B2 | 7/2013 | Orth |
| 8,714,977 B2 | 5/2014 | Fromovich et al. |
| 8,899,984 B2 | 12/2014 | Llop et al. |
| 8,968,002 B2 | 3/2015 | Purga et al. |
| 9,011,146 B2 | 4/2015 | Suttin et al. |
| 2003/0061679 A1 | 4/2003 | Chang et al. |
| 2004/0219477 A1 | 11/2004 | Harter |
| 2005/0100863 A1 | 5/2005 | Chang |
| 2006/0121410 A1 | 6/2006 | Aravena |
| 2006/0147880 A1 | 7/2006 | Krumsiek et al. |
| 2006/0188840 A1* | 8/2006 | Verban, Jr. ............. A61C 1/084 433/75 |
| 2008/0119895 A1 | 5/2008 | Manceau |
| 2009/0130630 A1 | 5/2009 | Suttin et al. |
| 2009/0202959 A1 | 8/2009 | Ajlouni et al. |
| 2010/0173259 A1 | 7/2010 | Vogel et al. |
| 2010/0311006 A1* | 12/2010 | Lancieux ............... A61C 1/084 433/75 |
| 2012/0191103 A1 | 7/2012 | Jorneus et al. |
| 2012/0237898 A1 | 9/2012 | Palti et al. |
| 2012/0237899 A1 | 9/2012 | Holmstrom et al. |
| 2012/0295225 A1 | 11/2012 | Fromovich et al. |
| 2013/0089834 A1 | 4/2013 | Fromovich et al. |
| 2013/0095451 A1 | 4/2013 | Menzel et al. |
| 2013/0203018 A1 | 8/2013 | Marotta |
| 2013/0209956 A1 | 8/2013 | Sanders |
| 2013/0316306 A1 | 11/2013 | Carden et al. |
| 2014/0106305 A1 | 4/2014 | Jacoby et al. |
| 2014/0205970 A1 | 7/2014 | Courvoisier et al. |
| 2014/0242545 A1 | 8/2014 | Brun |
| 2014/0377718 A1 | 12/2014 | Korten et al. |
| 2015/0056573 A1 | 2/2015 | Collins et al. |
| 2015/0125822 A1 | 5/2015 | Cramer Von Clausbruch |
| 2015/0230896 A1 | 8/2015 | Korten et al. |
| 2015/0351878 A1 | 12/2015 | Honig |
| 2016/0015483 A1 | 1/2016 | Kumar et al. |
| 2016/0038254 A1 | 2/2016 | Prestipino |
| 2016/0062346 A1 | 3/2016 | Akmakjian |
| 2016/0081771 A1 | 3/2016 | Fromovich et al. |
| 2016/0128811 A1 | 5/2016 | Rauh et al. |
| 2016/0213452 A1 | 7/2016 | Simmons, Jr. |
| 2017/0007375 A9 | 1/2017 | Fromovich et al. |
| 2017/0239021 A1 | 8/2017 | Klein et al. |
| 2018/0140378 A1* | 5/2018 | Ebrahimi ............. A61C 1/0061 |
| 2018/0177567 A1 | 6/2018 | Klein et al. |

FOREIGN PATENT DOCUMENTS

| | | |
|---|---|---|
| WO | 2010010029 | 1/2010 |
| WO | 2010/025191 | 3/2010 |
| WO | 2016/043578 | 3/2016 |

OTHER PUBLICATIONS

An Office Action dated Aug. 14, 2019, which issued during the prosecution of U.S. Appl. No. 15/845,103.

do Nascimento, Cassio, and Rubens Ferreira de Albuquerque Jr. "Bacterial leakage along the implant-abutment interface." Implant Dentistry—The Most Promising Discipline of Dentistry. InTech, 2011.

Sahiwal Indira G., et al. "Macro design morphology of endoseous dental implants." The Journal of prosthetic dentistry 87.5 (2002): 543-551.

Eraslan, Oğuz, and Özgür İnan. "The effect of thread design on stress distributien in a solid screw implant: a 3D finite element analysis." Clinical oral investigations 14.4 (2010): 411-416.

U.S. Appl. No. 62/298,593, filed Feb. 23, 2016.

An Office Action dated Jan. 8, 2018, which issued during the prosecution of U.S. Appl. No. 15/440,462.

An Office Action dated Aug. 31, 2018, which issued during the prosecution of U.S. Appl. No. 15/440,462.

An Office Action dated Aug. 16, 2018, which issued during the prosecution of U.S. Appl. No. 15/845,103.

U.S. Appl. No. 62/438,031, filed Dec. 22, 2016.

An Office Action dated Jan. 31, 2019, which issued during the prosecution of U.S. Appl. No. 15/906,081.

Paltop Digital Fully Guided Surgical System brochure, published Nov. 2017.

* cited by examiner

DRILL GUIDE

CROSS REFERENCE TO RELATED APPLICATIONS

The present application is related to U.S. Ser. No. 15/845,103 to Klein et al., filed Dec. 18, 2017, published as US 2018/0177567 to Klein (now abandoned), and entitled "Drill Guide," which claims the priority of U.S. 62/438,031 to Klein, filed Dec. 22, 2016, and which is incorporated herein by reference.

FIELD OF THE INVENTION

The present invention relates to centering and guiding a dental drill bit for drilling into a patient's bone.

SUMMARY OF THE INVENTION

Apparatus is provided for use with a dental handpiece, an oral surgical guide, and a bushing disposed in the oral surgical guide. The apparatus comprises a rigid guide-sleeve and a drill bit having a shank. The shank is typically inserted into the rigid guide-sleeve to couple to the dental handpiece when the rigid guide-sleeve is coupled to the dental handpiece such that a lumen of the guide-sleeve and the drill bit are coaxial along a central longitudinal axis of the drill bit. In accordance with some applications of the present invention, an inner diameter of the guide-sleeve is at least 0.03 mm and/or less than 0.06 mm (e.g., 0.03-0.06 mm) greater than a diameter of the shank of the drill bit, thereby providing close proximity between the shank of the drill bit and the rigid guide-sleeve into which the shank is inserted to couple to the dental handpiece. For example, the inner diameter of the guide-sleeve may be at least 0.04 mm and/or less than 0.05 mm (e.g., 0.04-0.05 cm) greater than a diameter of the shank of the drill bit.

The guide-sleeve is sized and shaped to slide into the bushing, which is disposed the oral surgical guide. Upon the guide-sleeve being advanced into the bushing, the dental handpiece is forced to align the central longitudinal axis of the drill bit to be coaxial with the central longitudinal axis of the bushing.

In addition, for some applications, the apparatus further comprises a kit in which the drill bit, e.g., a first drill bit, and the rigid guide-sleeve are disposed, in addition to at least one additional drill bit. Typically, the diameter of the shank of the additional drill bit is the same as the diameter of the shank of the first drill bit, while the diameter of the cutting portion of the additional drill bit is not the same as the diameter of the cutting portion of the first drill bit.

There is therefore provided, in accordance with some applications of the present invention, apparatus for use with a dental handpiece, an oral surgical guide, and a bushing disposed in the oral surgical guide, the apparatus including:
  a drill bit having a shank;
  a rigid guide-sleeve having a proximal end and a distal end and a lumen extending from the proximal end to the distal end,
    the proximal end of the guide-sleeve being removably couplable to a distal end of the dental handpiece, such that the lumen of the guide-sleeve and the drill bit when coupled to the distal end of the dental handpiece are coaxial along a central longitudinal axis of the drill bit, an inner diameter of the guide-sleeve being 0.03-0.06 mm greater than a diameter of the shank of the drill bit, and
    the distal end of the guide-sleeve being sized and shaped to be slidably couplable with the bushing, such that upon the guide-sleeve being advanced into the bushing, the dental handpiece is forced to align the central longitudinal axis of the drill bit to be coaxial with a central longitudinal axis of the bushing.

For some applications, the apparatus further includes a kit in which the drill bit and the guide-sleeve are disposed, and the drill bit is a first drill bit, and the kit includes at least one additional drill bit, a diameter of a shank of the additional bit is the same as the diameter of the shank of the first drill bit, and a diameter of a cutting portion of the additional drill bit is not the same as a diameter of a cutting portion of the first drill bit.

For some applications, an inner diameter of the guide-sleeve is 3-6 mm.

For some applications, an outer diameter of the guide-sleeve is 3.5-6.5 mm.

For some applications, an inner diameter of the guide-sleeve is 3-6 mm, an outer diameter of the guide-sleeve is 3.5-6.5 mm, and the outer diameter is 0.5-1.5 mm larger than the inner diameter.

For some applications, when the guide-sleeve and drill bit are coupled to the distal end of the dental handpiece, a distance between a distal tip of the drill bit and the distal end of the guide-sleeve is between 5 mm and 35 mm.

For some applications, the guide-sleeve is configured to be immovable with respect to the drill bit when the guide-sleeve and drill bit are coupled to the distal end of the dental handpiece and the drill bit is not rotating.

For some applications, the guide-sleeve is shaped to define an opening to accommodate irrigation flow from an irrigation channel of the dental handpiece.

For some applications, the apparatus further includes one or more protrusions, protruding from the proximal end of the guide-sleeve.

For some applications, the guide-sleeve is configured to prevent the drill bit from contacting the bushing when (a) the guide-sleeve and drill bit are coupled to the distal end of the dental handpiece, and (b) the guide-sleeve is in the bushing.

There is further provided, in accordance with some applications of the present invention, apparatus for use with a dental handpiece, a drill bit having a shank, an oral surgical guide, and a bushing disposed in the oral surgical guide, the apparatus including:
  a rigid guide-sleeve having a proximal end and a distal end and a lumen extending from the proximal end to the distal end,
    the proximal end of the guide-sleeve being removably couplable to a distal end of the dental handpiece, such that the lumen of the guide-sleeve and the drill hit when coupled to the distal end of the dental handpiece are coaxial along a central longitudinal axis of the drill bit, an inner diameter of the guide-sleeve being 2.38-2.41 mm, and
    the distal end of the guide-sleeve being sized and shaped to be slidably couplable with the bushing, such that upon the guide-sleeve being advanced into the bushing, the dental handpiece is forced to align the central longitudinal axis of the drill bit to be coaxial with a central longitudinal axis of the bushing.

For some applications, the inner diameter of the guide-sleeve is 2.39-2.40 mm.

The present invention will be more fully understood from the following detailed description of applications thereof, taken together with the drawings, in which:

DETAILED DESCRIPTION

Figure 1:
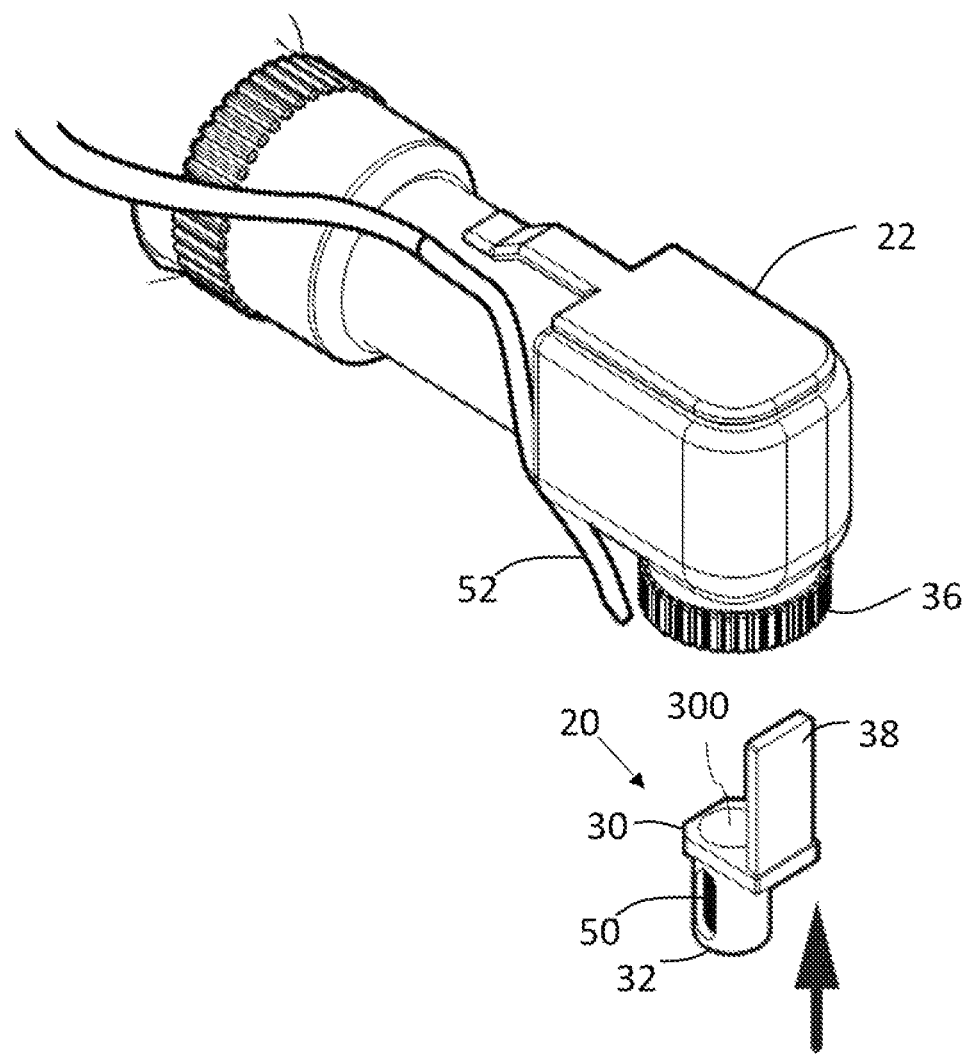
FIG. 1 is an exploded schematic illustration of a guide-sleeve and a dental handpiece, in accordance with an application of the present invention.
Figure 2A:
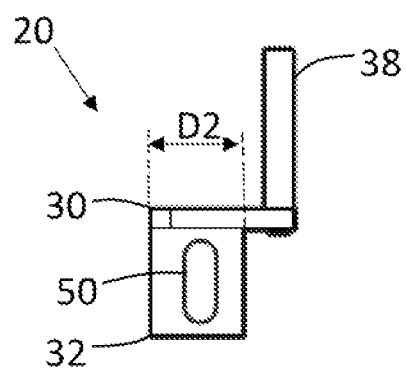
FIGS. 2A-D are schematic illustrations of different views of the guide-sleeve for use with a dental handpiece, drill bit, bushing, and oral surgical guide, in accordance with an application of the present invention.
Figure 2B:
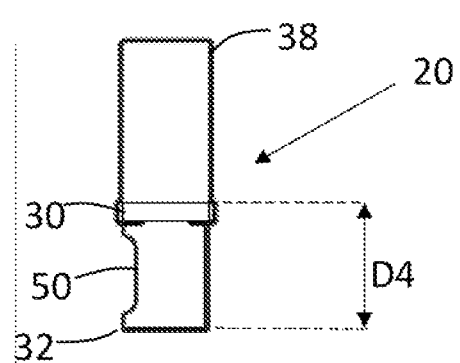
Figure 2C:
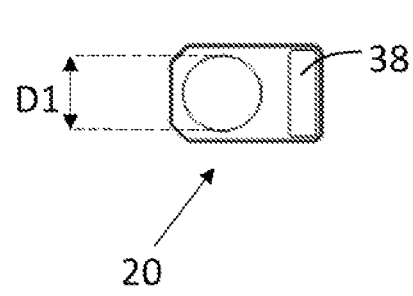
Figure 2D:
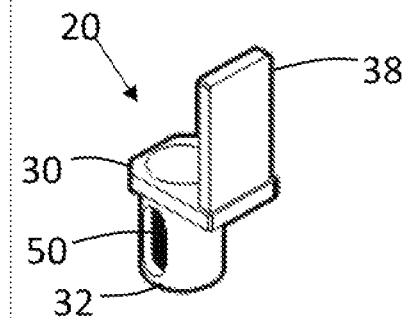
Figure 9:
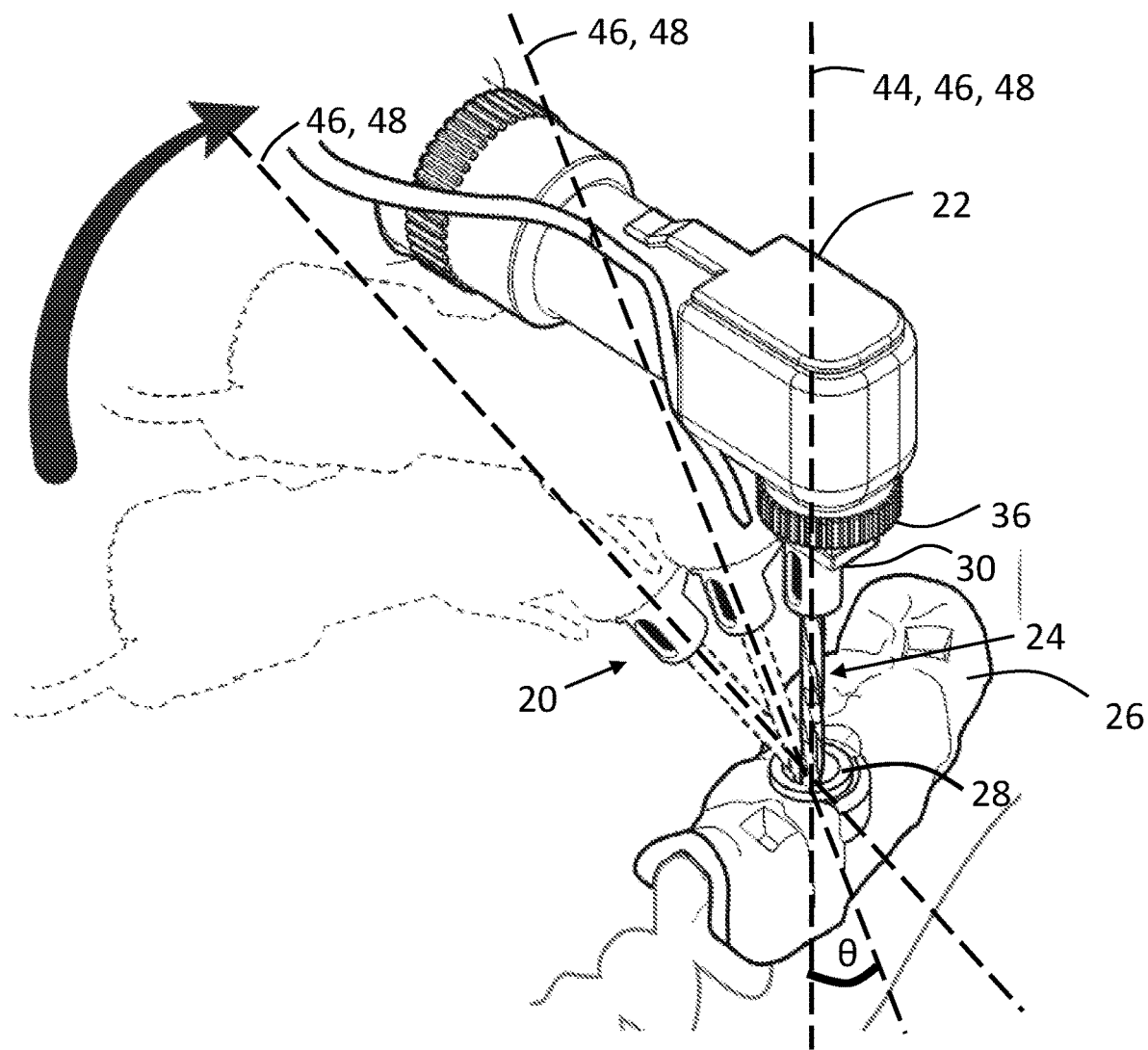
FIG. 9 is a schematic illustration of movement of the guide-sleeve and drill bit, both coupled to the dental handpiece, where the distal tip of the drill bit is in the bushing, in accordance with an application of the present invention.

Reference is made to FIGS. 1 and 9. FIG. 1 is an exploded schematic illustration of a guide-sleeve 20 for use with a dental handpiece 22, in accordance with some applications of the present invention. FIG. 9 is a schematic illustration of guide-sleeve 20 being used with a drill bit 24, an oral surgical guide 26, and a bushing 28 disposed in oral surgical guide 26, in accordance with some applications of the present invention. Guide-sleeve 20 has a proximal end 30 and a distal end 32 and a lumen 300 extending from the proximal end to the distal end. Proximal end 30 of guide-sleeve 20 is removably couplable to a distal end 36 of dental handpiece 22, such that the lumen of guide-sleeve 20 and drill bit 24 (FIG. 4) when coupled to distal end 36 of dental handpiece 22, are coaxial along a central longitudinal axis 46 of drill bit 24.

As used in the present application, including in the claims, a "dental handpiece" is to be understood as referring to the handpiece of a dental drilling instrument.

As used in the present application, including in the claims, a "central longitudinal axis" of an elongate structure is the set of all centroids of transverse cross-sectional sections of the structure along the structure. Thus, the cross-sectional sections are locally perpendicular to the central longitudinal axis, which runs along the structure. (If the structure is circular in cross-section, the centroids correspond with the centers of the circular cross-sectional sections.)

Figure 8:
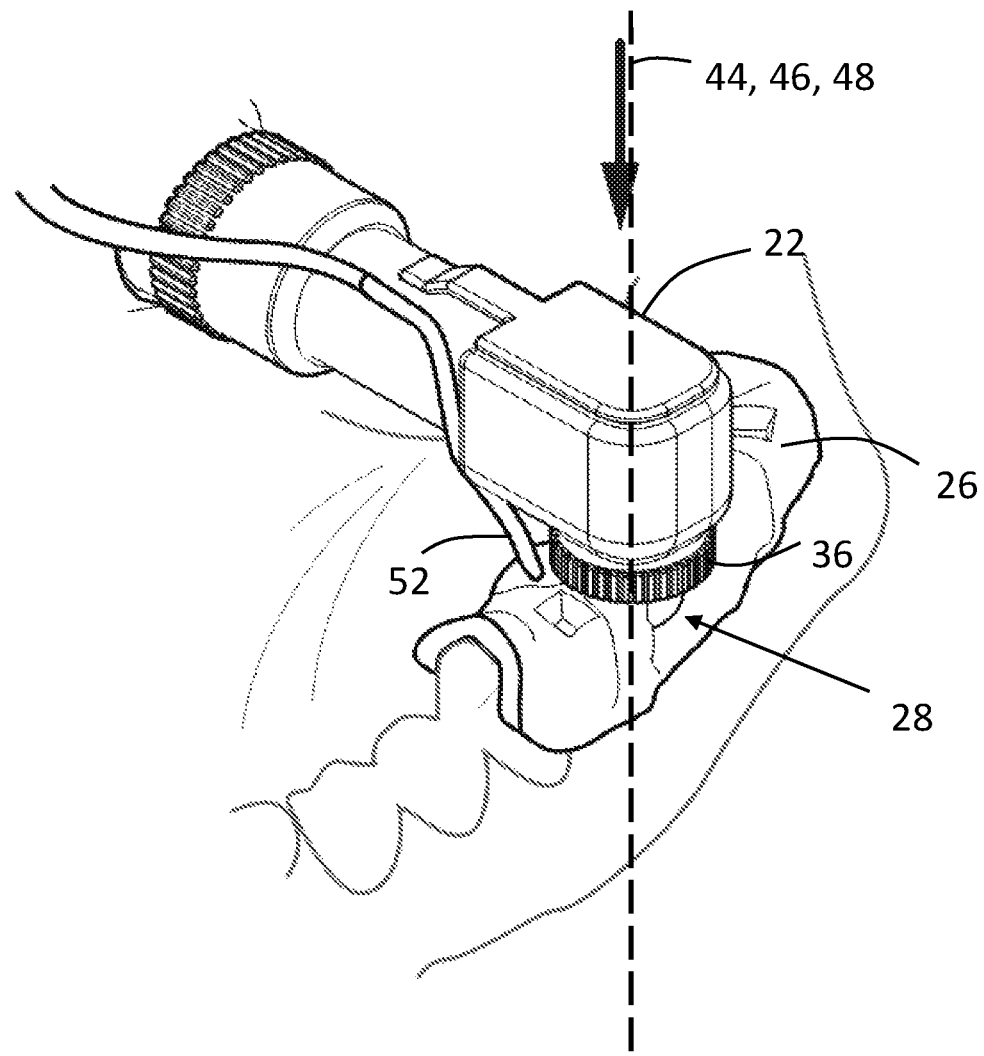
FIG. 8 is a schematic illustration of the guide-sleeve coupled to the dental handpiece, where the guide-sleeve is fully inside the bushing, in accordance with an application of the present invention.

Distal end 32 of guide-sleeve 20 is sized and shaped to be slidably couplable with bushing 28, as shown in FIGS. 8 and 9, such that upon guide-sleeve 20 being advanced into bushing 28, dental handpiece 22 is forced to align central longitudinal axis 46 of drill bit 24 to be coaxial with a central longitudinal axis 44 of bushing 28.

Reference is made to FIGS. 2A-D, which are schematic illustrations of guide-sleeve 20, in accordance with some applications of the present invention.

Figure 6:
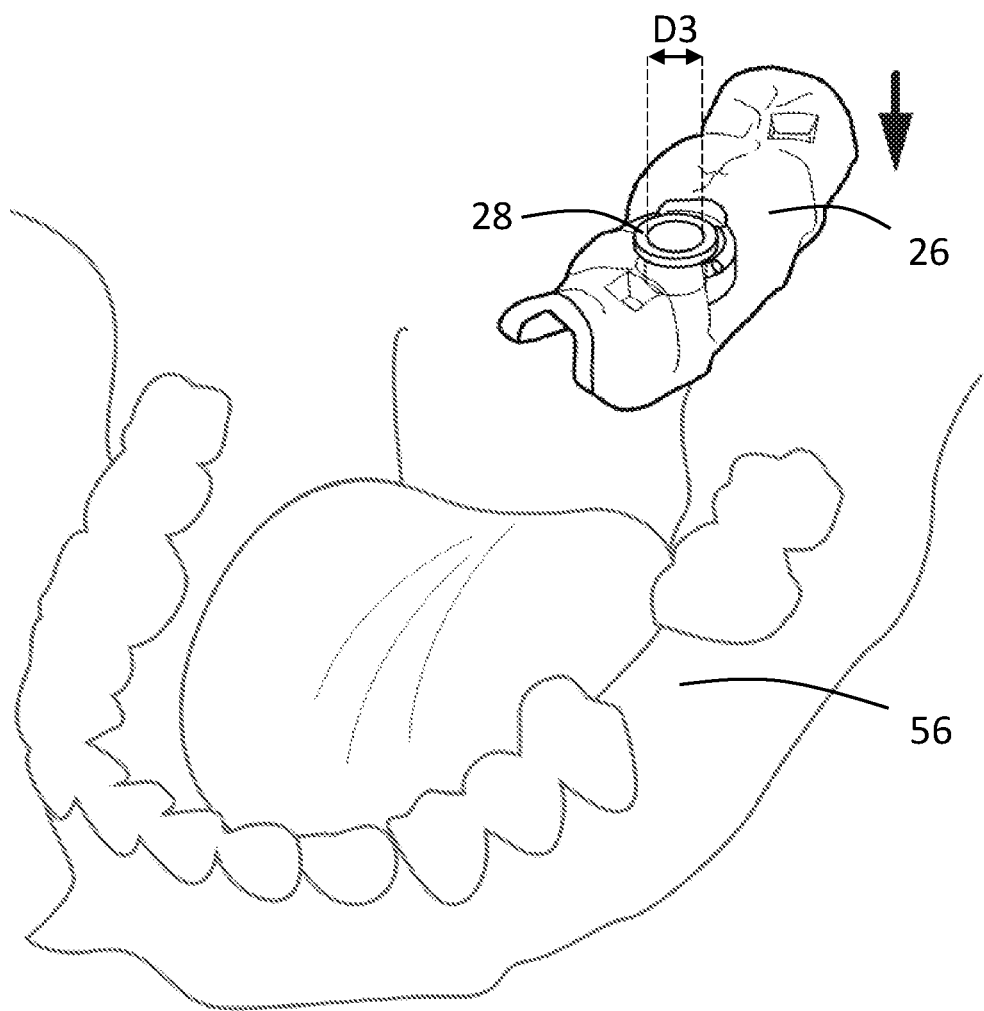
FIG. 6 is an exploded schematic illustration of the bushing and oral surgical guide suspended above an implant site, in accordance with an application of the present invention.
Figure 7:
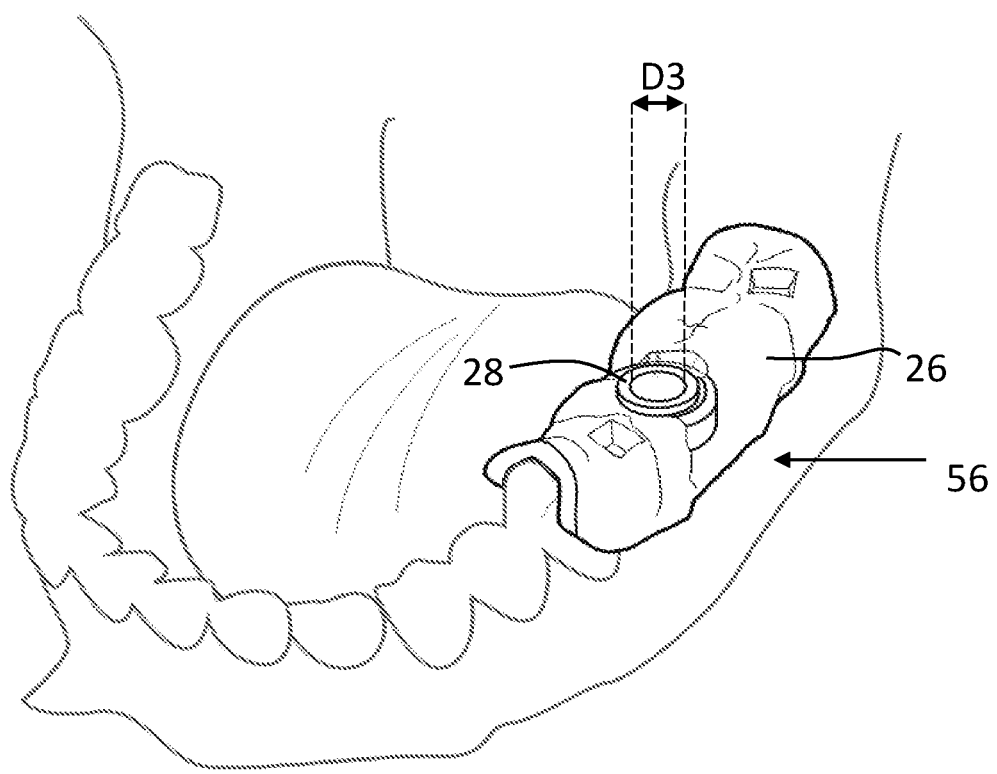
FIG. 7 is a schematic illustration of the bushing and oral surgical guide positioned on the implant site, in accordance with an application of the present invention.

For some applications, the dimensions of guide-sleeve 20 are set using one or more of the following options:

- Guide-sleeve 20 is typically sized and shaped such that an inner diameter D1 of guide-sleeve 20 is at least 2 mm and/or less than 6 mm (e.g., at least 3 mm and/or less than 6 mm), an outer diameter D2 of guide-sleeve 20 is at least 3.5 mm and/or less than 6.5 mm, and outer diameter D2 of guide-sleeve 20 is 0.5-1.5 mm larger than inner diameter D1;
- The height D4 of guide-sleeve 20 is typically at least 5 mm and/or less than 10 mm;
- Inner diameter D1 of guide-sleeve 20 is typically at least 0.03 mm and/or less than 0.06 mm (e.g., 0.03-0.06 mm, e.g. 0.04-0.05 mm) greater than a diameter D5 of a shank 40 of drill bit 24, as shown in FIG. 3; and/or
- Outer diameter D2 of guide-sleeve 20 typically within 100 microns of an inner diameter D3 of bushing 28, as shown in FIGS. 6 and 7.

In an application of the present invention, guide-sleeve 20 comprises at least one protrusion 38, protruding from the proximal end 30 of guide-sleeve 20. Protrusion 38 is configured to lockingly engage a corresponding hole (not shown) in distal end 36 of dental handpiece 22. For some applications, guide-sleeve 20 comprises one or more protrusions 38 (configuration not shown), protruding from proximal end 30 of guide-sleeve 20.

Figures 3A, 3B:
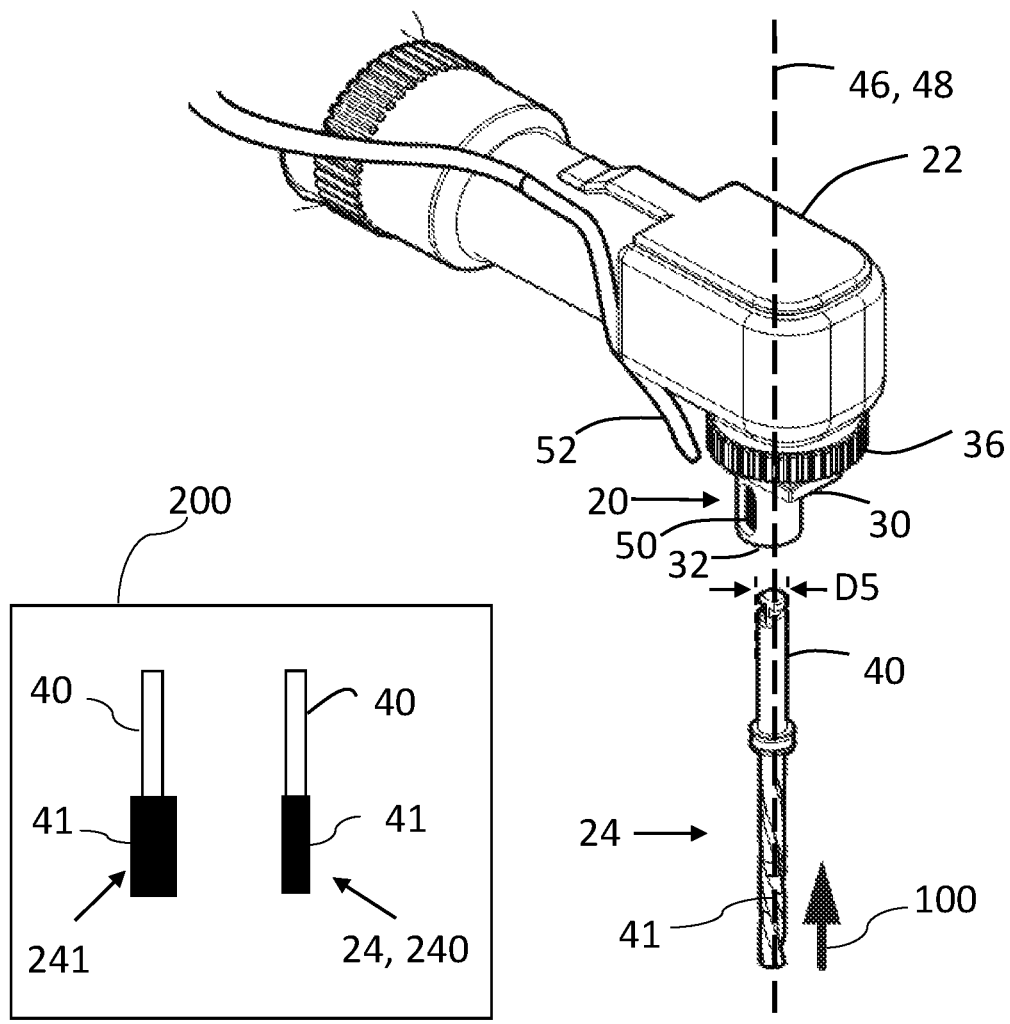
FIGS. 3A-B are schematic illustrations of the guide-sleeve coupled to the dental handpiece, and a kit for holding drill bits, in accordance with an application of the present invention.

Reference is now made to FIG. 3A, which is a schematic illustration of the apparatus, in which guide-sleeve 20 is coupled to distal end 36 of dental handpiece 22, and drill bit 24 is shown suspended below distal end 36 of dental handpiece 22 so as to show how drill bit 24 is inserted into distal end 36 of dental handpiece 22. Guide-sleeve 20 and drill bit 24 are aligned such that a central longitudinal axis 48 of guide-sleeve 20 is coaxial with central longitudinal axis 46 of drill bit 24. As shown in FIG. 3A, and indicated by arrow 100, drill bit 24 is coupled to distal end 36 of dental handpiece 22 by being inserted into guide-sleeve 20 when guide-sleeve 20 is coupled to distal end 36 of dental handpiece 22.

Figure 4:
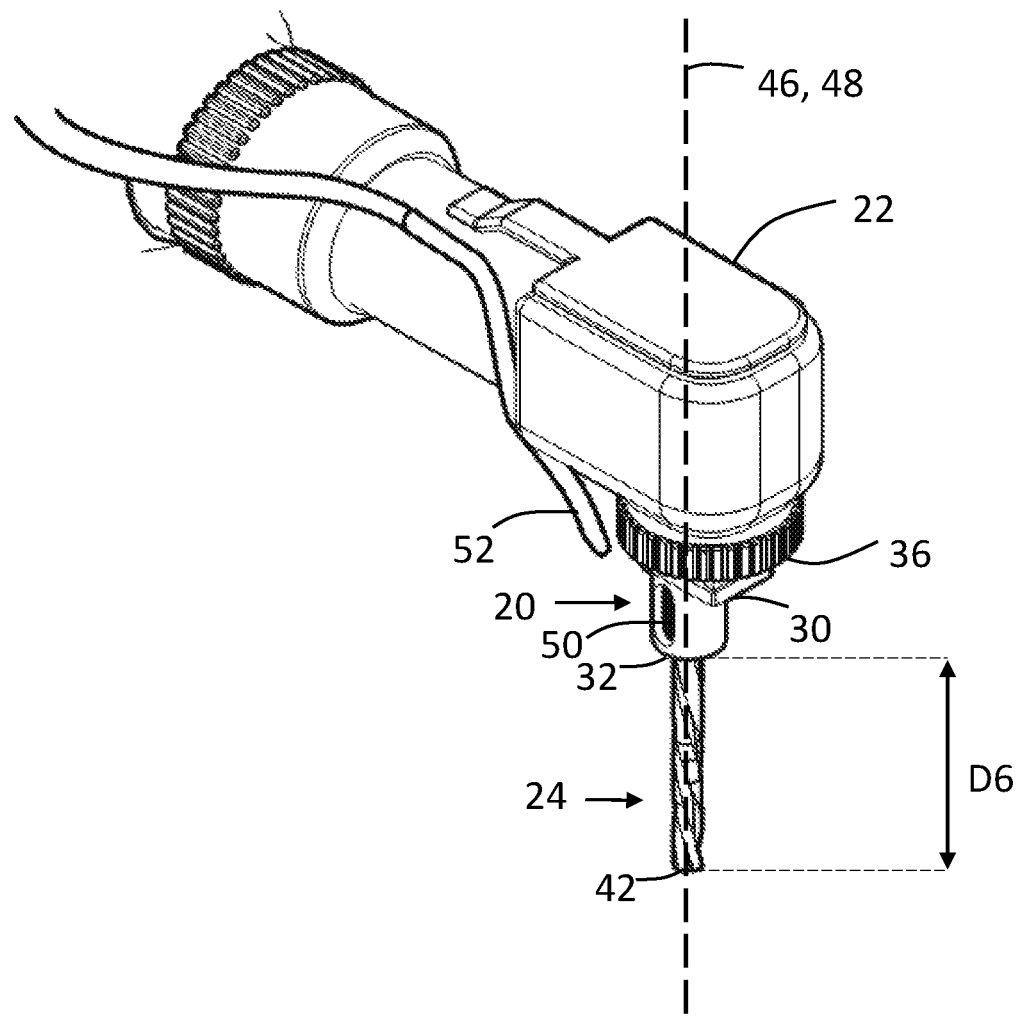
FIG. 4 is a schematic illustration of the guide-sleeve and &rill bit, both coupled to the dental handpiece, in accordance with an application of the present invention.

Reference is now made to FIG. 4, which is a schematic illustration of the apparatus in which guide-sleeve 20 and drill bit 24 are coupled to distal end 36 of dental handpiece 22. Guide-sleeve 20 is configured to be immovable with respect to drill bit 24 when guide-sleeve 20 and drill bit 24 are coupled to distal end 36 of dental handpiece 22 and the drill bit is not rotating.

A distance D6 between a distal tip 42 of drill bit 24 and distal end 32 of guide-sleeve 20 is typically at least 5 mm and/or less than 35 mm when guide-sleeve 20 and drill bit 24 are coupled to distal end 36 of dental handpiece 22.

Reference is now made to FIGS. 2-4. As shown in FIG. 2C, guide-sleeve 20 has an inner diameter D1, and as shown in FIG. 3, shank 40 has a diameter D5. Shank 40 is inserted through lumen 300 of guide-sleeve 20, thereby coupling drill bit 24 to dental handpiece 22. Typically, inner diameter D1 of guide-sleeve 20 is 0.03-0.06 mm greater than a diameter D5 of shank 40 of drill bit 24. For example, if diameter D5 of shank 40 is 2.350 mm, as is typical for many conventional drill bits, the inner diameter D1 of guide-sleeve 20 is 2.38-2.41 mm, e.g., 2.39-2.40 mm.

Typically, the proximity between guide-sleeve 20 and shank 40 of drill bit 24 provides stability of drill bit 24 with respect to guide-sleeve 20, and in turn to dental handpiece 22, in a manner that, on the one hand, provides enough of a gap between the shank and the guide-sleeve in order to allow free rotation of the drill bit, and on the other hand, enhances stability of the rotation of the drill bit. Typically, the close proximity between guide-sleeve 20 and drill bit 24 reduces wobbling of drill bit 24, and thus improves rotation, repeatability, and performance of the drill bit.

Additionally, the close tolerance between guide-sleeve 20 and shank 40 of drill bit 24 typically preserves proper drilling functionality of drill bit 24 over time, even over multiple uses of dental handpiece 22. Typically, over multiple uses, it can be expected that some moving parts in dental handpiece 22 (e.g., a chuck that engages shank 40, ball bearings, etc.) undergo degradation due to multiple uses of the dental handpiece. Degradation of moving parts in dental handpiece 22 may therefore result in degradation of the rotation mechanism in dental handpiece 22, causing imprecise rotation and wobbling of drill bit 24.

The proximity between the substantially-stationary guide-sleeve 20 and the rotating shank 40 typically preserves firm and stable rotation of the drill bit, regardless of any degradation of moving parts in dental handpiece 22. Typically, there is generally no relative movement of guide-sleeve 20 with respect to dental handpiece 22, so any degradation of moving parts that may occur in dental handpiece 22 has no substantial effect on the coupling of guide-sleeve 20 to dental handpiece 22. In particular, there is generally no movement between dental handpiece 22 and protrusion 38 which is lockingly engaged into dental handpiece 22.

Drill bit 24 is shaped to define shank 40 and cutting portion 41. For some applications, drill bit 24 is a first drill bit 240 and an additional drill bit 241 is provided. (e.g., in a kit 200 shown in FIG. 3B). For some applications, the diameter of the shank of additional drill bit 241 is the same as diameter D5 of shank 40 of the first drill bit, and a diameter of a cutting portion of the additional drill bit is not the same as a diameter of a cutting portion of the first drill bit (FIG. 3B). For example, the diameter of a cutting portion of the additional drill bit may be up to around two or three times larger than the diameter of the first drill bit. Typically, this allows fitting drill bits with varying cutting portion diameters but the same shank diameter to guide-sleeve 20.

Figure 5:
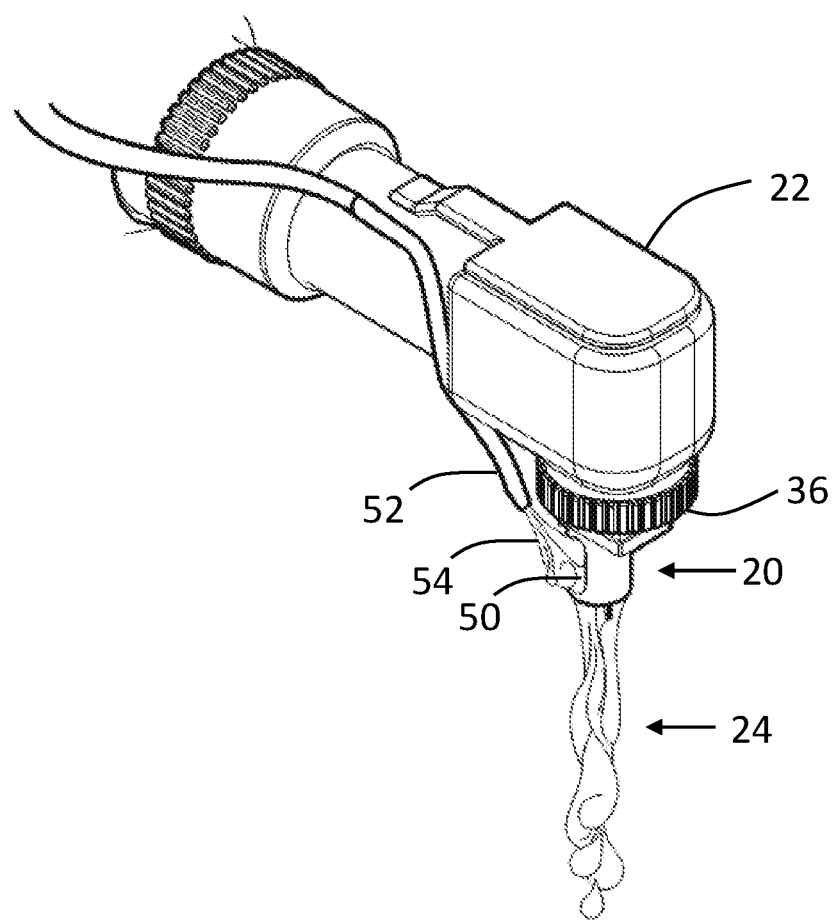
FIG. 5 is a schematic illustration of an irrigation channel on the dental handpiece and an opening in the guide-sleeve to accommodate an irrigation flow, in accordance with an application of the present invention.

Reference is now made to FIG. 5, which is a schematic illustration of the apparatus, in which guide-sleeve 20 and drill bit 24 are shown to be coupled to distal end 36 of dental handpiece 22. Guide-sleeve 20 is shaped to define an opening 50 to accommodate an irrigation flow 54 from an irrigation channel 52 on dental handpiece 22. Typically, guide-sleeve 20 is configured to remain stationary during rotation of drill bit 24 when guide-sleeve 20 is coupled to distal end 36 of dental handpiece 22.

Reference is now made to FIGS. 6-7, which are schematic illustrations of bushing 28, disposed in oral surgical guide 26. Oral surgical guide 26 is shown suspended above an implant site 56 in FIG. 6 and positioned on implant site 56 in FIG. 7.

Reference is now made to FIG. 8, which is a schematic illustration of guide-sleeve 20 and drill bit 24 coupled to distal end 36 of dental handpiece 22, where guide-sleeve 20 is fully inside bushing 28, aligned such that a central longitudinal axis 48 of guide-sleeve 20 is coaxial with central longitudinal axis 44 of bushing 28. (Guide-sleeve 20 and drill bit 24 are not visible, as they are inside oral surgical guide 26.) Guide-sleeve 20 prevents drill bit 24 from contacting bushing 28, when guide-sleeve 20 and drill bit 24 are coupled to distal end 36 of dental handpiece 22 and when guide-sleeve 20 is in bushing 28.

Reference is now made to FIG. 9, which is a schematic illustration of movement of guide-sleeve 20 and drill bit 24, both coupled to dental handpiece 22, where distal tip 42 of drill bit is in bushing 28, in accordance with an application of the present invention. For some applications, a method is provided for aligning drill bit 24 with bushing 28 in oral surgical guide 26. The method comprises placing distal tip 42 of drill bit 24 into bushing 28 at an angle theta, such that the smaller of the two angles formed between central longitudinal axis 46 of drill bit 24 and central longitudinal axis 44 of bushing 28 is typically at least 5 degrees and/or less than 45 degrees. Subsequently, the dentist aligns central longitudinal axis 48 of guide-sleeve 20 to be coaxial with central longitudinal axis 44 of bushing 28, as shown in FIG. 3. Aligning central longitudinal axis 48 of guide-sleeve 20 with central longitudinal axis 44 of bushing 28 forces dental handpiece 22 to reorient, in turn forcing central longitudinal axis 46 of drill bit 24 to be coaxial with central longitudinal axis 44 of the bushing 28. Once drill bit 24 is aligned, it can be advanced into the tissue of the patient. In some applications, angle theta is typically at least 5 degrees and/or less than 25 degrees.

It is noted that by providing the dentist with the ability to initially place drill bit 24 in bushing 28 at angle theta allows the patient to open her mouth less wide, and thus reduces discomfort of the patient during the procedure and/or allows the performance of a procedure in a case where it would be difficult for the patient to open her mouth sufficiently wide.

For some applications, dental apparatus useful in procedures such as those described hereinabove is assembled by coupling guide-sleeve 20 to distal end 36 of dental handpiece 22, and coupling drill bit 24 to distal end 36 of dental handpiece 22, such that central longitudinal axis 46 of drill bit 24 is coaxial with central longitudinal axis 48 of guide-sleeve 20, as shown in FIG. 3 and FIG. 4.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. A system comprising:
   a dental handpiece;
   an oral surgical guide;
   a bushing configured to be disposed in the oral surgical guide;
   a drill bit having a shank; and
   a rigid guide-sleeve having a proximal end and a distal end and a lumen extending from the proximal end to the distal end,
   (A) comprising one or more protrusions, protruding from the proximal end of the guide-sleeve and configured to lockingly engage a corresponding hole in a distal end of the dental handpiece,
   (B) the proximal end of the guide-sleeve being removably couplable to the distal end of the dental handpiece, such that the lumen of the guide- sleeve and the drill bit when coupled to the distal end of the dental handpiece are coaxial along a central longitudinal axis of the drill bit, an inner diameter of the guide-sleeve being 0.03-0.06 mm greater than a diameter of the shank of the drill bit, and

(C) the distal end of the guide-sleeve being sized and shaped to be slidably couplable with the bushing, such that upon the guide-sleeve being advanced into the bushing, the dental handpiece is forced to align the central longitudinal axis of the drill bit to be coaxial with a central longitudinal axis of the bushing.

2. The system according to claim 1, further comprising a kit in which the drill bit and the guide-sleeve are disposed, wherein the drill bit is a first drill bit, wherein the kit comprises at least one additional drill bit, wherein a diameter of a shank of the additional drill bit is the same as the diameter of the shank of the first drill bit, and wherein a diameter of a cutting portion of the additional drill bit is not the same as a diameter of a cutting portion of the first drill bit.

3. The system according to claim 1, wherein an inner diameter of the guide-sleeve is 3-6 mm.

4. The system according to claim 1, wherein an outer diameter of the guide-sleeve is 3.5-6.5 mm.

5. The system according to claim 1, wherein an inner diameter of the guide-sleeve is 3-6 mm, an outer diameter of the guide-sleeve is 3.5-6.5 mm, and the outer diameter is 0.5-1.5 mm larger than the inner diameter.

6. The system according to claim 1, wherein when the guide-sleeve and drill bit are coupled to the distal end of the dental handpiece, a distance between a distal tip of the drill bit and the distal end of the guide-sleeve is between 5 mm and 35 mm.

7. The system according to claim 1, wherein the guide-sleeve is configured to be immovable with respect to the drill bit when the guide-sleeve and drill bit are coupled to the distal end of the dental handpiece and the drill bit is not rotating.

8. The system according to claim 1, wherein the guide-sleeve is shaped to define an opening to accommodate irrigation flow from an irrigation channel of the dental handpiece.

9. The system according to claim 1, wherein the guide-sleeve is configured to prevent the drill bit from contacting the bushing when (a) the guide-sleeve and drill bit are coupled to the distal end of the dental handpiece, and (b) the guide-sleeve is in the bushing.

10. A system comprising:
a dental handpiece;
an oral surgical guide;
a bushing configured to be disposed in the oral surgical guide;
a drill bit having a shank; and
a rigid guide-sleeve having a proximal end and a distal end and a lumen extending from the proximal end to the distal end,
(A) comprising one or more protrusions, protruding from the proximal end of the guide-sleeve and configured to lockingly engage a corresponding hole in a distal end of the dental handpiece,
(B) the proximal end of the guide-sleeve being removably couplable to the distal end of the dental handpiece, such that the lumen of the guide-sleeve and the drill bit when coupled to the distal end of the dental handpiece are coaxial along a central longitudinal axis of the drill bit, an inner diameter of the guide-sleeve being 2.38-2.41 mm, and
(C) the distal end of the guide-sleeve being sized and shaped to be slidably couplable with the bushing, such that upon the guide-sleeve being advanced into the bushing, the dental handpiece is forced to align the central longitudinal axis of the drill bit to be coaxial with a central longitudinal axis of the bushing.

11. The system according to claim 10, wherein the inner diameter of the guide-sleeve is 2.39-2.40 mm.

* * * * *